(12) United States Patent
Kokate et al.

(10) Patent No.: US 6,579,243 B2
(45) Date of Patent: Jun. 17, 2003

(54) CATHETER WITH THERMAL SENSOR FOR DETECTION OF VULNERABLE PLAQUE

(75) Inventors: Jaydeep Y. Kokate, Maple Grove, MN (US); Eric M. DoBrava, Crystal, MN (US); Suzana Prstic, Minneapolis, MN (US); Scott Kimmell, St. Paul, MN (US); Marwane S. Berrada, Minneapolis, MN (US); Avram Bar-Cohen, St. Louis Park, MN (US); Michael Hoey, Shoreview, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 30 days.

(21) Appl. No.: 09/797,400

(22) Filed: Mar. 1, 2001

(65) Prior Publication Data

US 2001/0047138 A1 Nov. 29, 2001

Related U.S. Application Data

(60) Provisional application No. 60/186,524, filed on Mar. 2, 2000.

(51) Int. Cl.$^7$ .................................................. A61B 5/00
(52) U.S. Cl. ..................... 600/549; 600/474; 604/96.01
(58) Field of Search ..................... 604/96.01, 101.01, 604/101.03, 101.05, 104, 164.1; 600/473, 474, 549, 585, 433–435

(56) References Cited

U.S. PATENT DOCUMENTS

| | | | |
|---|---|---|---|
| 5,275,594 A | 1/1994 | Baker et al. ................... 606/12 |
| 5,293,868 A | 3/1994 | Nardella ...................... 600/373 |
| 5,309,910 A | 5/1994 | Edwards et al. ............. 600/381 |
| 5,431,806 A | * 7/1995 | Suzuki et al. ................ 204/415 |
| 5,433,216 A | * 7/1995 | Sugrue et al. ............... 600/591 |
| 5,445,157 A | 8/1995 | Adachi et al. ............... 600/474 |
| 5,498,261 A | 3/1996 | Strul ............................ 606/29 |
| 5,542,915 A | 8/1996 | Edwards et al. ............... 604/22 |
| 5,599,346 A | 2/1997 | Edwards et al. ............... 604/41 |
| 5,871,449 A | 2/1999 | Brown ........................ 600/474 |
| 5,910,101 A | 6/1999 | Andrews et al. ................ 600/3 |
| 5,924,997 A | 7/1999 | Campell ...................... 600/549 |
| 5,935,075 A | 8/1999 | Casscells et al. ........... 600/474 |
| 6,123,675 A | * 9/2000 | Kreizman et al. ........... 600/549 |
| 6,162,184 A | * 12/2000 | Swanson et al. ............. 600/549 |
| 6,176,842 B1 | * 1/2001 | Tachibana et al. ............. 604/22 |
| 6,245,026 B1 | 6/2001 | Campbell et al. ........... 600/549 |
| 6,248,083 B1 | * 6/2001 | Smith et al. ................ 600/585 |

FOREIGN PATENT DOCUMENTS

| | | |
|---|---|---|
| EP | 0 566 861 A1 | 3/1993 |
| WO | WO 00/34534 | 6/2000 |

* cited by examiner

*Primary Examiner*—Max F. Hindenburg
*Assistant Examiner*—Charles Marmor, II
(74) *Attorney, Agent, or Firm*—Fish & Richardson P.C., P.A.

(57) ABSTRACT

Methods and devices for detecting vulnerable plaque within a blood vessel are disclosed. An elongate medical device in accordance with the present invention includes an elongate shaft having a proximal end and a distal end. A substrate is fixed to the elongate shaft proximate the distal end thereof, and a plurality of sensors are disposed on the substrate. Each sensor is preferably coupled to a switching device. The switching devices are preferably disposed on the substrate.

13 Claims, 8 Drawing Sheets

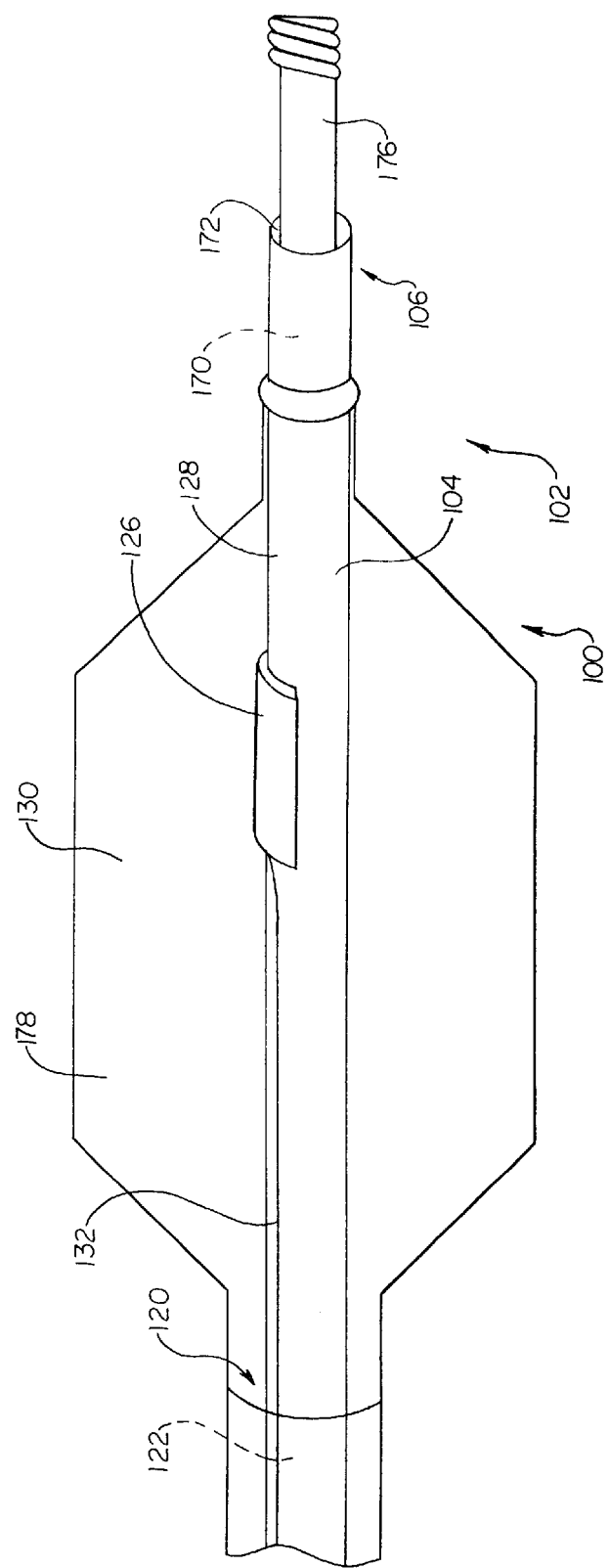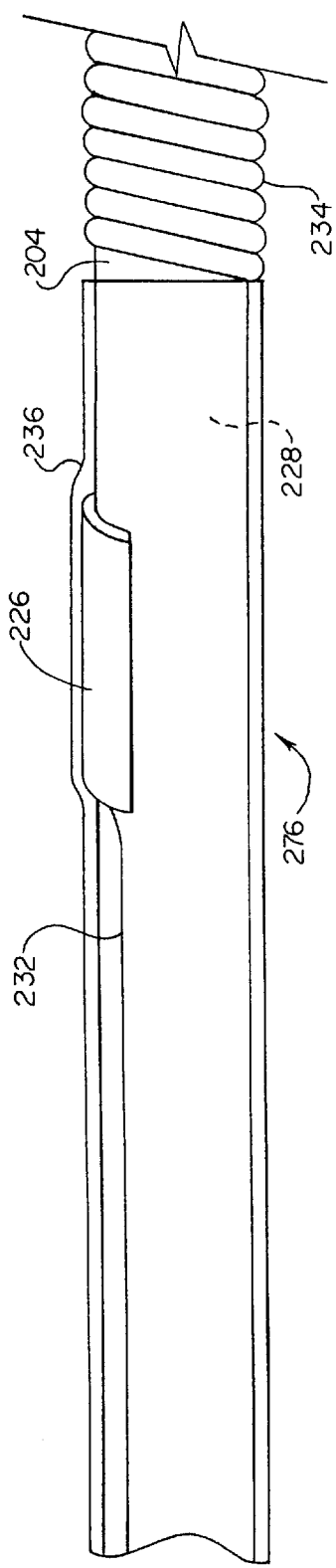

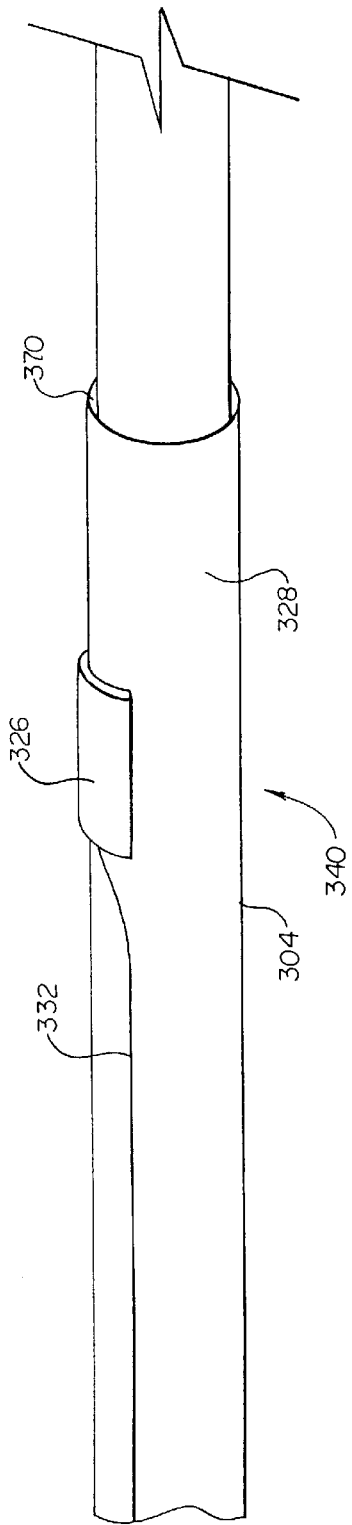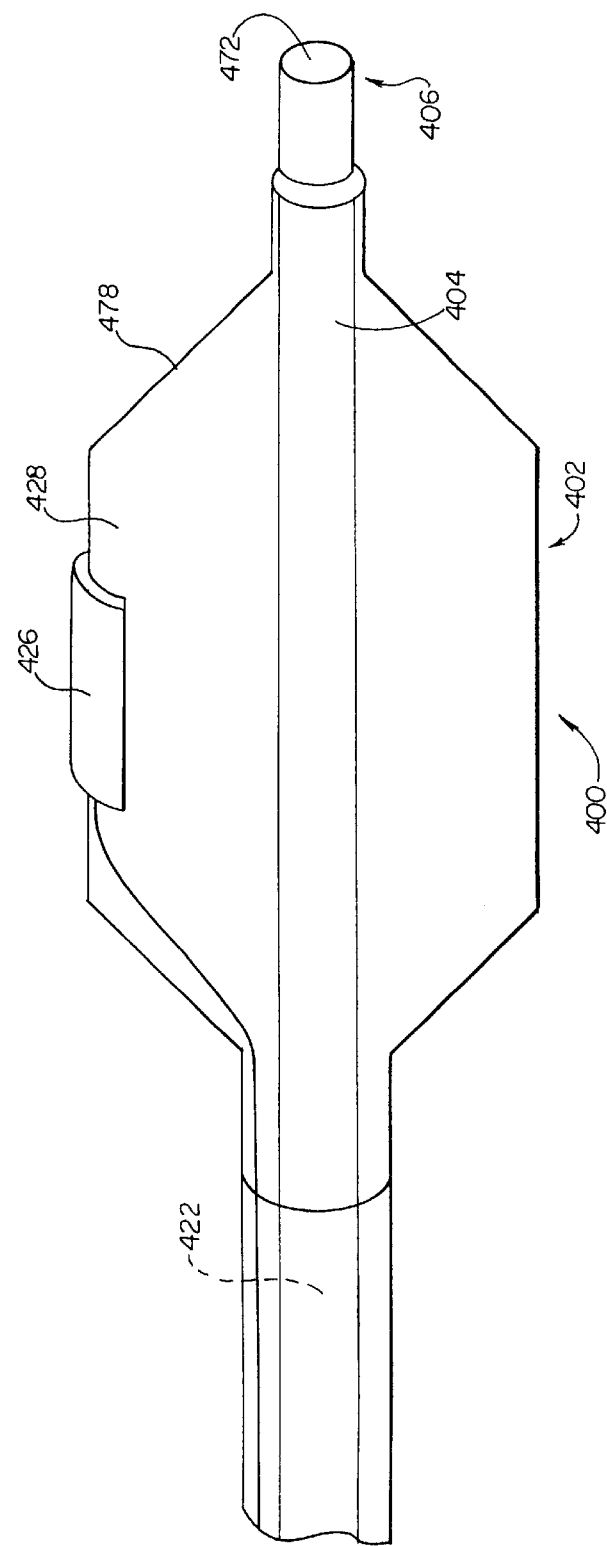

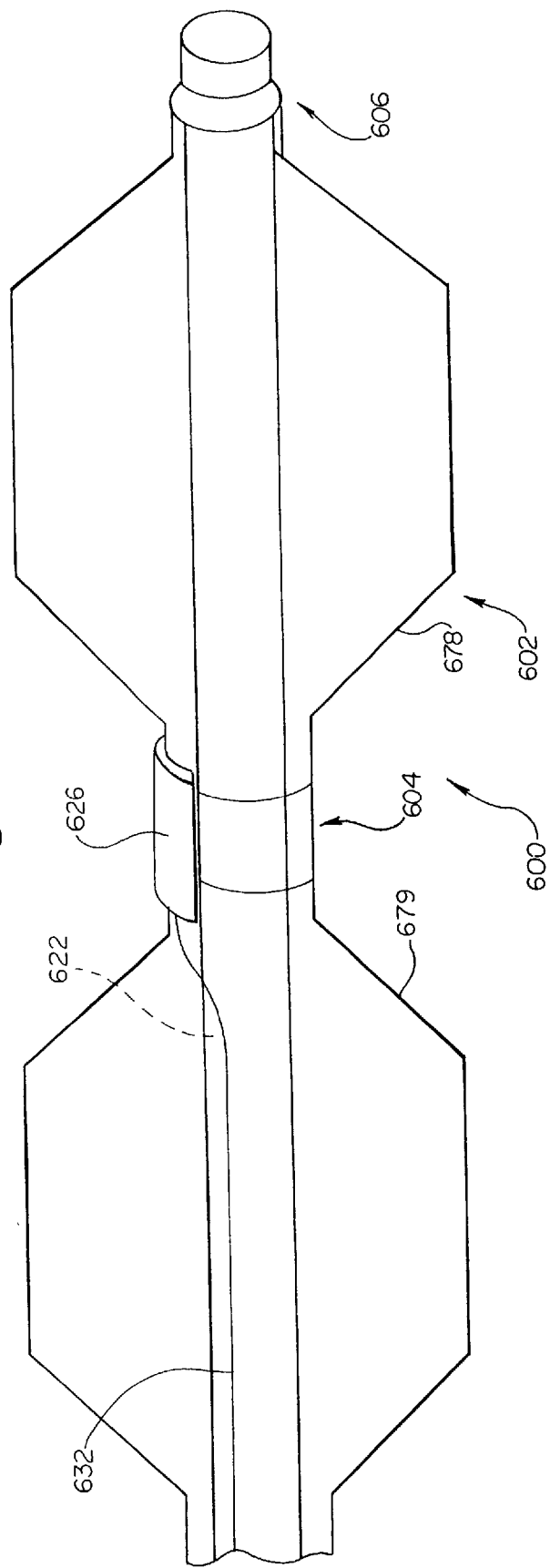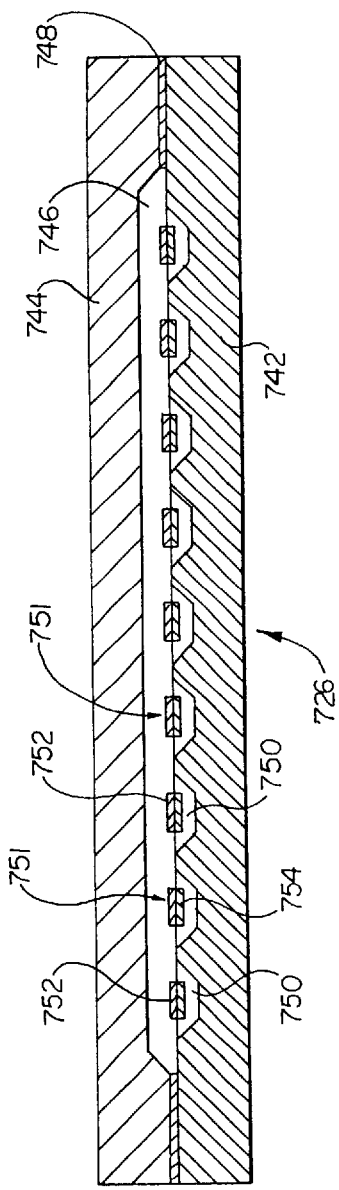

CATHETER WITH THERMAL SENSOR FOR DETECTION OF VULNERABLE PLAQUE

This application claims the benefit of Provisional Application Serial No. 60/186,524 filed Mar. 2, 2000.

FIELD OF THE INVENTION

The present invention relates generally to intravascular catheters. More particularly, the present invention relates to intravascular catheters adapted to make measurements within the body of a patient.

BACKGROUND OF THE INVENTION

Therapy modalities for heart disease have traditionally focused on treating blood vessels which have become occluded (blocked) or stenotic (narrowed) by calcified plaque deposits. Blood vessels that have become occluded or stenotic in this manner may interrupt the flow of blood that supplies oxygen to the heart muscle. Occluded or stenotic blood vessels may be treated with a number of medical procedures including angioplasty and atherectomy. Angioplasty techniques such as percutaneous transluminal angioplasty (PTA) and percutaneous transluminal coronary angioplasty (PTCA) are relatively non-invasive methods of treating restrictions in blood vessels. In these procedures, a balloon catheter is advanced over a guidewire until the balloon is positioned proximate a restriction in a diseased vessel. The balloon is then inflated and the restriction in the vessel is opened. During an atherectomy procedure, the stenotic lesion is mechanically cut or abraded away from the blood vessel wall using an atherectomy catheter.

Calcified plaque deposits typically comprise hard materials. Plaque may also comprise soft materials or combinations of soft and hard materials. Soft plaque typically comprises deposits of cholesterol and other fats which build up within the blood vessels as a patient ages. The build up of plaque in the blood vessels is sometimes referred to as atherosclerosis, or hardening of the arteries.

Atherosclerosis often begins as a small injury to an artery wall. This injury triggers a cyclic cascade of injury and response, inflammation, and healing, which may ultimately lead to the narrowing of the artery. As the atherosclerotic plaque worsens, inflammatory cells, especially macrophages, collect at the site to isolate the debris of the damaged tissue. The result is a core of lipid, macrophages or foam cells and nectrotic tissue, covered by a fibrous cap of scar tissue. If the fibrous cap becomes weakened or is subjected to excessive stress, it may rupture, exposing the thrombogenic contents of the core to the blood stream. If the resulting blood clot is severe enough, it may occlude the artery. If this obstruction persists in a coronary artery, a myocardial infarction may result.

Plaque deposits with a risk of rupturing are sometimes referred to as vulnerable plaque. Vulnerable plaque typically comprises a core of soft materials covered with a fibrous cap. Many vulnerable plaque deposits do not limit the flow of blood through the blood vessels. It has recently been appreciated that vulnerable plaques that do not limit flow may be particularly dangerous because they produce no warning symptoms, but can rupture suddenly causing heart attack and death. This may occur, for example, when the vulnerable plaque ruptures, forming a blood clot inside the blood vessel lumen and causing a blockage.

Recently, the pivotal role of inflammation in the progression of atherosclerosis has been recognized. A systemic increase in temperature is often associated with infection (e.g., a fever). Likewise, a local infection or localized damage to tissue may result in a localized increase in temperature. An increase in temperature is thought to be caused by the response of the immune system to infection, known as inflammation. It has been observed that the inflamed necrotic core of a vulnerable plaque maintains itself at a temperature that may be one or more degrees Celsius higher than that of the surrounding tissue. For example, an inflamed plaque in a human heart, where the normal temperature is about 37° C. may be at a temperature as high as 40° C.

SUMMARY OF THE INVENTION

The present invention is directed to methods and devices for the detection of vulnerable plaque within an artery. A device in accordance with one embodiment of the present invention includes an elongate shaft having a distal end and a proximal end. A detector assembly is fixed to the elongate shaft proximate the distal end thereof.

In one method in accordance with the present invention, a catheter including a detector assembly disposed within a balloon is provided. The catheter is advanced through the vasculature of a patient until a distal end of the catheter is proximate a target region of a vessel. The balloon of the catheter is then inflated, for example, with a gas. When the balloon is inflated, blood within the vessel is displaced. The detector assembly detects infrared radiation from the body of the patient. In a preferred method, the infrared radiation is absorbed by the detector assembly and converted to an electrical signal. The electrical signal is transmitted to an external display and/or recording device. In an additional method in accordance with the present invention, a bolometer is placed proximate a target tissue.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the Figures thereof and wherein:

FIG. 1 is a perspective view of a distal portion of a catheter in accordance with an exemplary embodiment of the present invention;

FIG. 2 is a perspective view of a guidewire in accordance with an exemplary embodiment of the present invention;

FIG. 3 is a perspective view of a device in accordance with an exemplary embodiment of the present invention;

FIG. 4 is a perspective view of a distal portion of a catheter in accordance with an exemplary embodiment of the present invention;

FIG. 6 is a perspective view of a distal portion of a catheter in accordance with an exemplary embodiment of the present invention;

FIG. 7 is a cross sectional view of a detector assembly in accordance with an exemplary embodiment of the present invention.

DETAILED DESCRIPTION OF THE INVENTION

Figure 5:
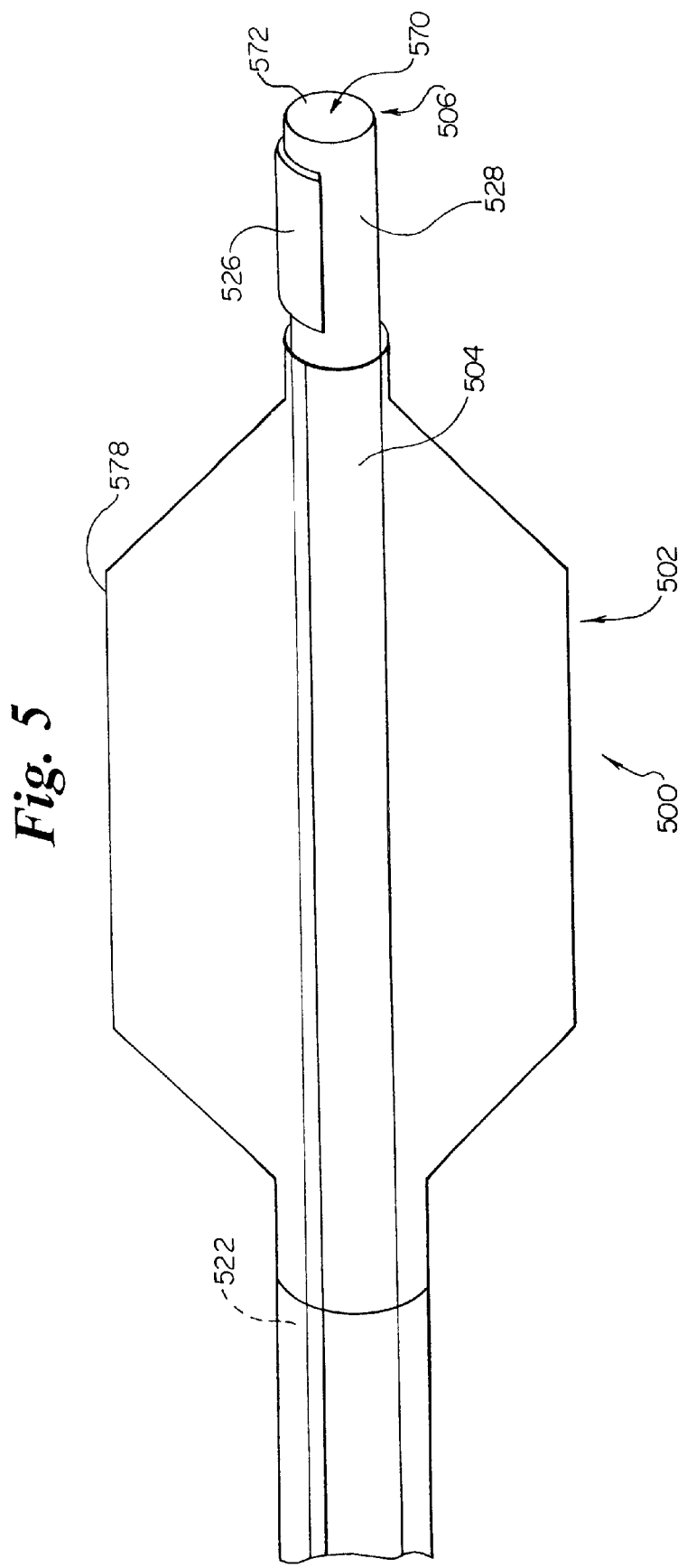
FIG. 5 is a perspective view of a distal portion of a catheter in accordance with an exemplary embodiment of the present invention.

The following detailed description should be read with reference to the drawings, in which like elements in different drawings are numbered in like fashion. The drawings which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives which may be utilized.

FIG. 1 is a perspective view of a distal portion 102 of a catheter 100 in accordance with the present invention. Catheter 100 includes an elongate shaft 104 having a distal end 106 and a proximal end (not shown). In the embodiment of FIG. 1, catheter 100 includes a distal guidewire port 172 disposed proximate distal end 106 of elongate shaft 104. Elongate shaft 104 includes a plurality of walls defining a guidewire lumen 170 that is in fluid communication with distal guidewire port 172 and a proximal guidewire port (not shown). A guidewire 176 is partially disposed within guidewire lumen 170. It is to be appreciated that catheter 100 may comprise various general types of catheters. Examples of catheter types include over-the-wire catheters and single operator exchange (SOE) catheters.

A balloon 178 is disposed about elongate shaft 104 proximate distal end 106 thereof. Elongate shaft 104 also includes a plurality of walls defining an inflation lumen 122. Elongate shaft 104 also defines an inflation orifice 120 that is in fluid communication with inflation lumen 122 and balloon 178. A fluid source (not shown) may be coupled proximate the proximal end (not shown) of catheter 100. Balloon 178 may be inflated by urging fluid from the fluid source (not shown) into balloon 178 via inflation lumen 122 and inflation orifice 120. For the purposes of this disclosure, the term fluid may refer to a liquid and/or a gas. In a preferred method associated with catheter 100 of FIG. 1, balloon 178 is inflated with a gas or liquid that is substantially transparent to infrared energy.

Catheter 100 of FIG. 1 is a type of catheter that may be generally referred to as a balloon catheter. It is to be appreciated that catheter 100 may comprise various general types of catheters. Examples of catheter types include percutaneous myocardial revascularization (PMR) catheters, atherectomy catheters, and stent delivery catheters.

Those of skill in the art will appreciate that elongate shaft 104 may comprise various materials without deviating from the spirit and scope of the present invention. Elongate shaft 104 may also be comprised of a single material, or a combination of materials. For example, elongate shaft 104 may include an inner tube. In a presently preferred embodiment, the inner tube is comprised of PTFE (polytetrafluoroethylene). PTFE is a preferred material because it creates a smooth, low-friction surface for the passage of other devices through the elongate shaft 104. Elongate shaft 104 may also include a support member, wound or braided around the inner tube. In a presently preferred embodiment, the support member is comprised of a plurality of filaments. The filaments may be stainless steel wire. Those with skill in the art will appreciate that other embodiments of a support member are possible without deviating from the spirit and scope of the present invention. For example, a support member may comprise a woven polymer fabric. By way of a second example, a support member may comprise polymer fibers wound in a braided pattern.

In a presently preferred embodiment, elongate shaft 104 comprises polyether block amide (PEBA). Polyether block amide is commercially available from Atochem Polymers of Birdsboro, Pennsylvania under the trade name PEBAX. Also in a presently preferred embodiment, elongate shaft 104 is fabricated using an extrusion process. In this process, molten PEBA may be extruded onto the combined layers of an inner tube and a support member. When this process is utilized, the extruded material fills any interstitial spaces in the support member.

It is to be understood that other manufacturing processes can be used without departing from the spirit and scope of the present invention. Elongate shaft 104 may also comprise other materials without departing from the spirit of scope of this invention. Examples of materials that may be suitable in some applications include: polyethylene (PE), polypropylene (PP), polyvinylchloride (PVC), polyurethane, and polytetrafluoroethylene (PTFE).

Catheter 100 also includes a detector assembly 126. In the embodiment of FIG. 1, detector assembly 126 is fixed to an outer surface 128 of elongate shaft 104. Also in the embodiment of FIG. 1, detector assembly 126 is disposed within a cavity 130 of balloon 178. A conductor 132 is coupled to detector assembly 126. Conductor 132 may include a plurality of signal paths. In the embodiment of FIG. 1, conductor 132 is partially disposed within inflation lumen 122 of elongate shaft 104.

In a preferred embodiment, detector assembly 126 comprises a plurality of infrared radiation sensors each having a low thermal mass. In a particularly preferred embodiment, detector assembly 126 comprises a microbolometer array fabricated utilizing micro electro mechanical machining (MEMS) fabrication processes (e.g., photolithographic processes). Also in a preferred embodiment, detector assembly 126 produces an electrical signal that is indicative of the infrared energy that impinges upon detector assembly 126. Several detector assemblies 126 may be disposed about elongate shaft 104. The output from each assembly can be separately monitored to determine the angular location of the plaque on the vessel wall. Alternately, a single detector assembly 126 could be used while shaft 104 is rotated in the vessel. Then the output of detector assembly 126 can be correlated with the angular position of detector assembly 126 to determine the angle location of the plaque on the vessel wall. These latter two options can also be utilized for the detector assemblies described below with respect to the alternate embodiments of the invention.

In a method in accordance with the present invention, distal end 106 of catheter 100 is advanced through the vasculature of a patient until distal portion 102 of catheter 100 is proximate a target region of a vessel. Balloon 178 is then inflated, for example, with a gas. When balloon 178 is inflated, it displaces blood within the vessel. Detector assembly 126 detects infrared radiation from the body of the patient. In a preferred method, detector assembly 126 is utilized to produce an electrical signal that is indicative of the infrared energy that impinges upon detector assembly 126. The electrical signal is transmitted to an external display and/or recording device via conductor 132.

FIG. 2 is a perspective view of a guidewire 276 in accordance with the present invention. Guidewire 276 includes an elongate shaft 204. A coil 234 is fixed to elongate shaft 204 proximate a distal end (not shown) thereof. A detector assembly 226 overlays an outer surface 228 of elongate shaft 204. A conductor 232 is coupled to detector assembly 226. Conductor 232 may include multiple signal conducting paths.

In the embodiment of FIG. 2, a sheath 236 is disposed about detector assembly 226, a portion of elongate shaft 204, and a portion of conductor 232. In a preferred embodiment, sheath 236 comprises shrink tubing. In a particularly preferred embodiment, sheath 236 comprises polytetrafluoroethylene (PTFE) shrink tubing. PTFE shrink tubing which may be suitable in some applications is commercially available Zeus Industries of Orangeburg, S.C. and Raychem Corporation of Menlo Park, Calif. Embodiments of guidewire 276 have been envisioned which do not include sheath 236.

FIG. 3 is a perspective view of device 340 in accordance with the present invention. Device 340 includes an elongate shaft 304 defining a guidewire lumen 370. A guidewire (not shown) is disposed within guidewire lumen 370. A detector assembly 326 is fixed to an outer surface 328 of elongate shaft 304. A conductor 332 is coupled to detector assembly 326. Conductor 332 may include multiple signal conducting paths.

FIG. 4 is a perspective view of a distal portion 402 of a catheter 400 in accordance with the present invention. Catheter 400 includes an elongate shaft 404 having a distal end 406 and a proximal end (not shown). In the embodiment of FIG. 4, catheter 400 includes a distal guidewire port 472 disposed proximate distal end 406 of elongate shaft 404. Elongate shaft 404 includes a plurality of walls defining a guidewire lumen (not shown) that is in fluid communication with distal guidewire port 472 and a proximal guidewire port (not shown). catheter 400 includes a distal guidewire port 472 disposed proximate distal end 406 of elongate shaft 404. Elongate shaft 404 includes a plurality of walls defining a guidewire lumen 470 that is in fluid communication with distal guidewire port 472 and a proximal guidewire port 474 (not shown).

Elongate shaft 404 also includes a plurality of walls defining an inflation lumen 422 in fluid communication with a balloon 478 that is disposed about elongate shaft 404. A fluid source (not shown) may be coupled proximate the proximal end (not shown) of catheter 400. Balloon 478 may be inflated by urging fluid from the fluid source (not shown) into balloon 478 via inflation lumen 422. Catheter 400 also includes a detector assembly 426. In the embodiment of FIG. 4, detector assembly 426 is fixed to an outer surface 428 of balloon 478. A conductor (not shown) is coupled to detector assembly 426. The conductor may include a plurality of signal paths.

In a method in accordance with the present invention, distal end 406 of catheter 400 is advanced through the vasculature of a patient until distal portion 402 of catheter 400 is proximate a target region of a vessel. Balloon 478 is then inflated, for example, with a gas. When balloon 478 is inflated, blood within the vessel is displaced and detector assembly 426 is placed in intimate contact with a portion of the vessel wall. Detector assembly 426 detects infrared radiation from the body of the patient. In a preferred method, detector assembly 426 produces an electrical signal that is indicative of the infrared energy that impinges upon detector assembly 426. The electrical signal is transmitted to an external display and/or recording device via the conductor.

FIG. 5 is a perspective view of a distal portion 502 of an additional embodiment of a catheter 500 in accordance with the present invention. Catheter 500 includes an elongate shaft 504 having a distal end 506 and a proximal end (not shown). In the embodiment of FIG. 5, catheter 500 includes a distal guidewire port 572 disposed proximate distal end 506 of elongate shaft 504. Elongate shaft 504 includes a plurality of walls defining a guidewire lumen 570 that is in fluid communication with distal guidewire port 572 and a proximal guidewire port (not shown).

A balloon 578 is disposed about elongate shaft 504. Elongate shaft 504 also includes a plurality of walls defining an inflation lumen 522 in fluid communication with balloon 578. A fluid source (not shown) may be coupled proximate the proximal end (not shown) of catheter 500. Balloon 578 may be inflated by urging fluid from the fluid source (not shown) into balloon 578 via inflation lumen 522.

Catheter 500 also includes a detector assembly 526. In the embodiment of FIG. 5, detector assembly 526 overlays an outer surface 528 of elongate shaft 504. A conductor (not shown) is coupled to detector assembly 526. The conductor may include a plurality of signal paths.

FIG. 6 is a perspective view of a distal portion 602 of an additional embodiment of a catheter 600 in accordance with the present invention. Catheter 600 includes an elongate shaft 604 having a distal end 606 and a proximal end (not shown). A first balloon 678 is disposed about elongate shaft 604 proximate distal end 606 thereof. A second balloon 679 is disposed about elongate shaft 604 proximally of first balloon 678.

Elongate shaft 604 includes a plurality of walls defining an inflation lumen 622 in fluid communication with first balloon 678 and second balloon 679. A fluid source (not shown) may be coupled proximate the proximal end (not shown) of catheter 600. First balloon 678 and second balloon 679 may be inflated by urging fluid from the fluid source (not shown) into both balloons 678 and 679 via inflation lumen 622. Embodiments of catheter 600 have been envisioned in which elongate shaft 604 includes a first inflation lumen and a second inflation lumen. In this envisioned embodiment, first balloon 678 and second balloon 679 may be selectively inflated.

Catheter 600 also includes a detector assembly 626. In the embodiment of FIG. 6, detector assembly 626 is disposed between first balloon 678 and second balloon 679. A conductor 632 is coupled to detector assembly 626. Conductor 632 may include a plurality of signal paths.

FIG. 7 is a cross sectional view of a detector assembly 726 in accordance with the present invention. Detector assembly 726 includes substrate 742 and a cover 744 that define a sensor array chamber 746. In a preferred embodiment, cover 744 is sealingly fixed to substrate 742 by a bond 748. Also in a preferred embodiment, sensor array chamber 746 is substantially filled with a gas having a low thermal conductivity. In a particularly preferred embodiment, sensor array chamber 746 contains a vacuum.

A plurality of pixels 751 are disposed on a top surface of substrate 742 of detector assembly 726 to obtain a thermal image of a strip of plaque and nearby vessel wall. In the embodiment of FIG. 7, each pixel comprises a sensing element 752 and a cavity 750 defined by substrate 742. In FIG. 7 it may be appreciated that each sensing element 752 is disposed above a cavity 750. In a preferred embodiment, each sensing element 752 comprises a thin film resistor. In the embodiment of FIG. 7, each sensing element 752 is supported by a beam 754. Disposing each sensing element 752 above a cavity 750 preferably thermally isolates the sensing elements 752 from the substrate 742.

Figure 8:
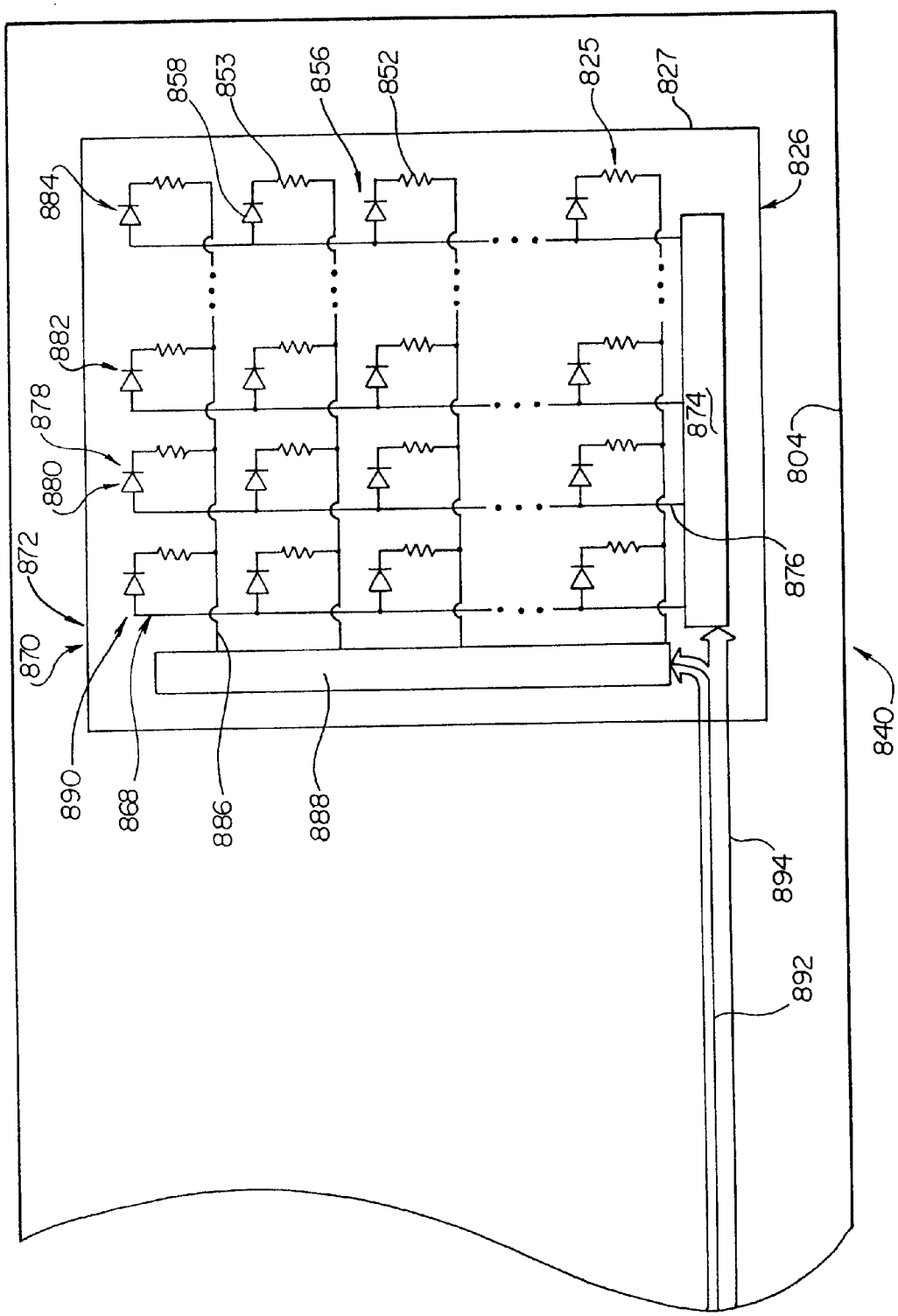
FIG. 8 is a diagrammatic representation of a device in accordance with an exemplary embodiment of the present invention.

FIG. 8 is a diagrammatic representation of a device 840 in accordance with the present invention. Device 840 includes an elongate shaft 804 and a detector assembly 826 fixed to an outer surface (not shown) of elongate shaft 804. Detector assembly 826 comprises a plurality of pixels 825 disposed on a substrate 827. Each pixel 825 comprises a sensing element 852 coupled to a switching device 856. In the embodiment of FIG. 8, each switching device 856 comprises a diode 858 and each sensing element 852 comprises a resistor 853. In a preferred embodiment each sensing element comprises a thin film resistor. Embodiments of detector assembly 826 are possible in which each switching device 856 comprises other elements, for example, transistors.

A first common conductor 868 is coupled to the switching devices 856 of a first group 870 of pixels 825. In the embodiment of FIG. 8, the pixels 825 of first group 870 form a first row 872. First common conductor 868 is also coupled to a group address circuit 874. Group address circuit 874 may be utilized to selectively activate the switching devices 856 of the pixels 825 of first group 870. A second common conductor 876 is also coupled to group address circuit 874.

Second common conductor 876 is coupled to the switching devices 856 of a second group 878 of pixels 825. Group address circuit 874 may selectively activate the switching devices 856 of pixels 825 of second group 878, for example by applying a voltage to second common conductor 876. In the embodiment of FIG. 8, the pixels 825 of second group 878 form a second row 880. Detector assembly 826 of FIG. 8 also includes a third row 882 and an Nth row 884, each row comprising a plurality of pixels 825 to obtain a thermal image of a strip of plaque and nearby vessel wall. It is to be appreciated that detector assembly 826 may comprise any number of pixels 825, and that these pixels may be arranged in any number of groups without deviating from the spirit and scope of the present invention.

In the embodiment of FIG. 8, a first interrogation conductor 886 is coupled to the first pixel 825 in each group. First interrogation conductor 886 is coupled to a sensor interrogation circuit 888. Sensor interrogation circuit 888 may be utilized to interrogate a sensing device 852 of a pixel 825. For example, group address circuit 874 may selectively activate the switching devices 856 of pixels 825 of first group 870, and sensor interrogation circuit 888 may selectively couple the sensing device 852 of a pixel {1,1} 890 to a readout conductor 892. Readout conductor 892 is preferably coupled to a measurement instrument that is adapted to assess the current state of a sensing device 852. In FIG. 8 it may be appreciated that a bus 894 is coupled to sensor interrogation circuit 888 and group address circuit 874. Bus 894 may include any number of conductors. These conductors may be used, for example, to communicate command signals between group address circuit 874 and a measurement instrument.

Figure 9:
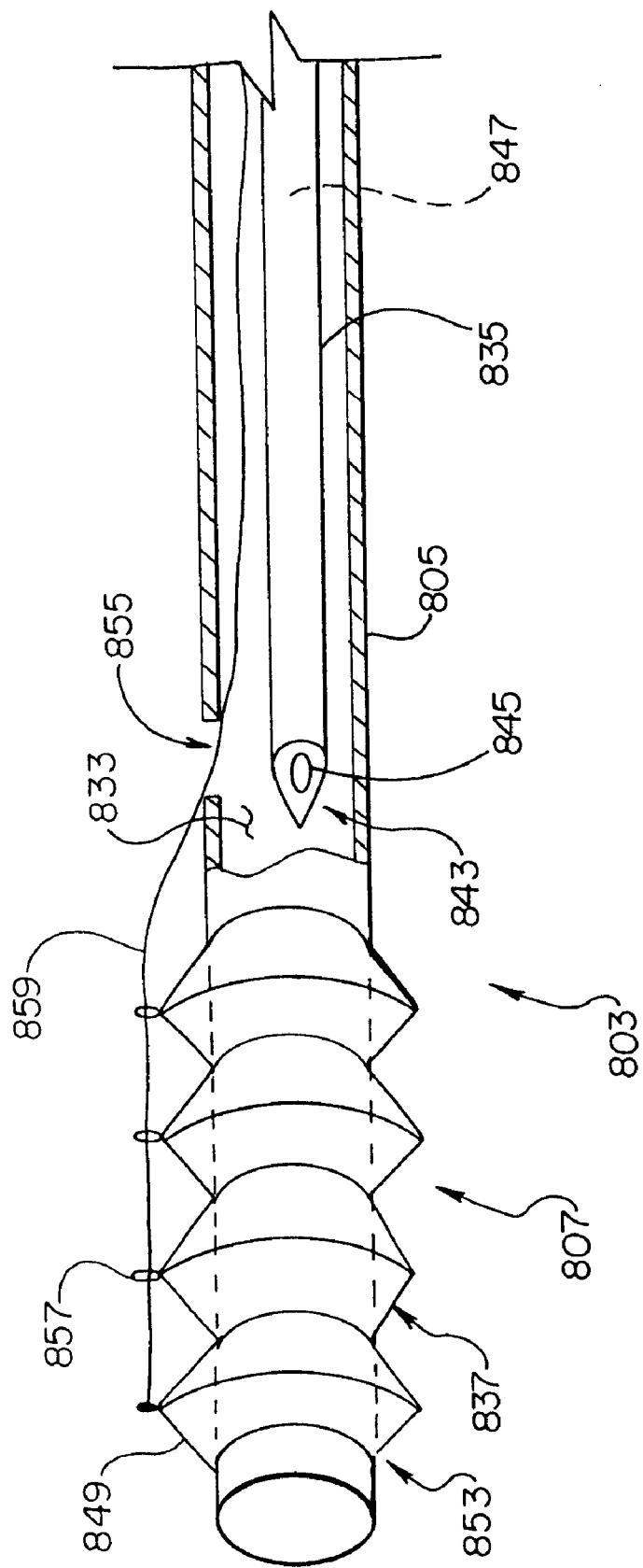
FIG. 9 is a partial cross sectional view of a therapeutic catheter in accordance with an additional embodiment of the present invention.

FIG. 9 is a partial cross sectional view of a therapeutic catheter 803 in accordance with an additional embodiment of the present invention. Once a plaque deposit is located, therapeutic catheter 803 may be used, for example, to inject lipid/plaque stabilizing drugs into the plaque deposit. Therapeutic catheter 803 comprises an outer shaft 805 and a laterally flexible portion 807 that is fixed to a distal end of outer shaft 805. In the embodiment of FIG. 9, laterally flexible portion 807 comprises a bellows 837.

Therapeutic catheter 803 includes a catheter lumen 833 defined by outer shaft 805 and bellows 837. In FIG. 9, an inner shaft 835 is shown slidingly disposed in catheter lumen 833. In the embodiment of FIG. 9, inner shaft 835 forms a point 843 proximate the distal end thereof. Inner shaft 835 defines an injection port 845 proximate point 843 and an injection lumen 847 in fluid communication with injection port 845. In a preferred embodiment, injection port 845 may be fluidly coupled to a fluid source via injection lumen 847. Fluid from the fluid source may be injected into a plaque deposit by piercing the outer portion of the deposit with point 843 so that injection port 845 is disposed within a core of the plaque deposit. Fluid from the fluid source may then be urged through injection lumen 847 and injection port 845. The fluid injected into the plaque deposit may preferably include lipid/plaque stabilizing drugs.

In FIG. 9, it may be appreciated that bellows 837 comprises a wall 849 forming a plurality of corrugations 853. In the embodiment of FIG. 9, a plurality of hoops 857 are fixed to bellows 837. A pull wire 859 is shown in FIG. 9 extending through hoops 857 and an aperture 855 defined by outer shaft 805. A distal end of pull wire 859 is fixed to laterally flexible portion 807 of therapeutic catheter 803 distally of hoops 857. A proximal portion of pull wire 859 preferably extends proximally beyond a proximal end of outer shaft 805. Pull wire 859 may preferably be used to change the shape of laterally flexible portion 807 of therapeutic catheter 803. In a preferred embodiment, laterally flexible portion 807 of therapeutic catheter 803 may have a generally straight shape as shown in FIG. 9, and may selectively have a generally curved shape.

Figure 10:
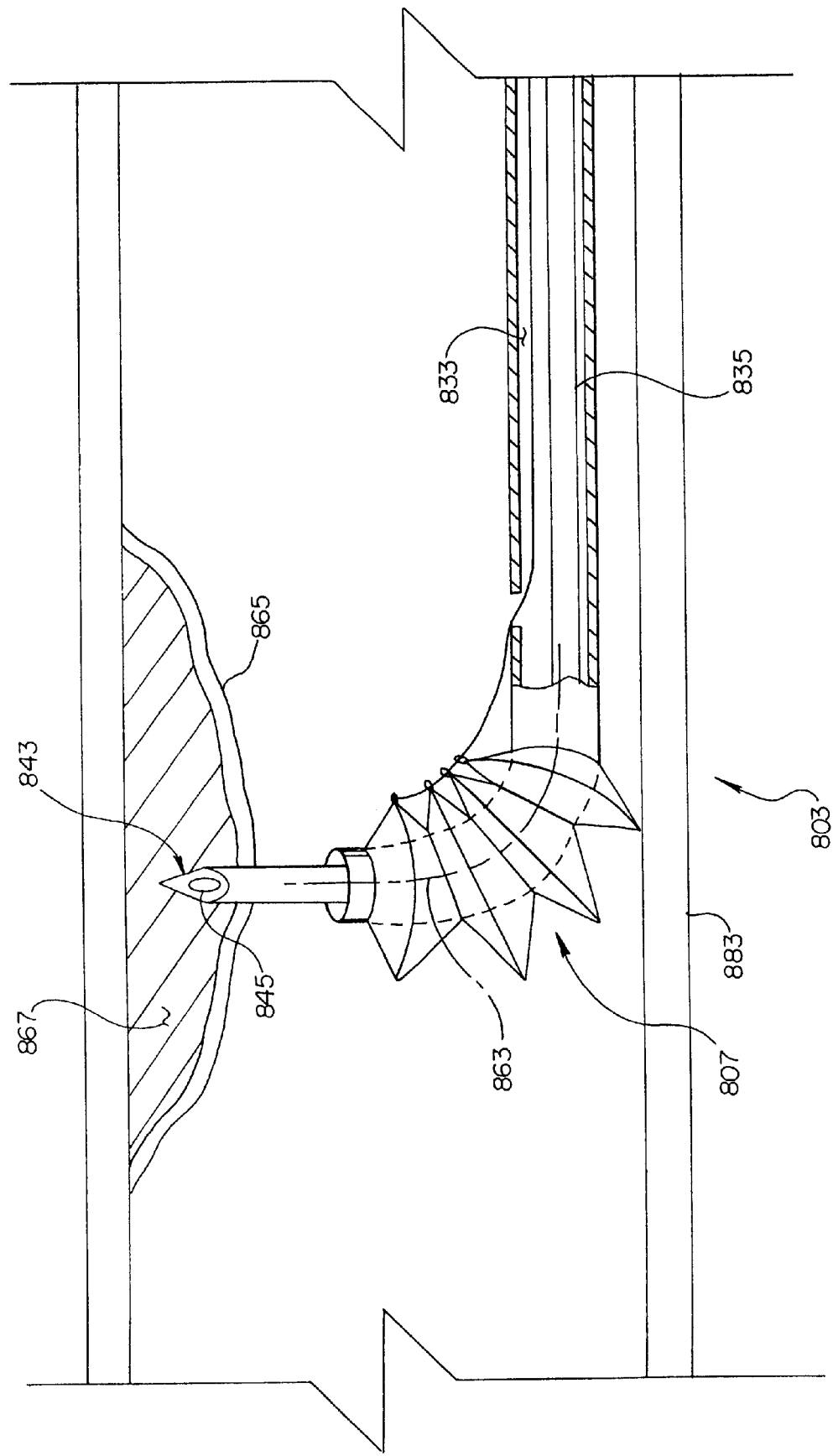
FIG. 10 is an additional partial cross sectional view of the therapeutic catheter of FIG. 9.

FIG. 10 is an additional partial cross sectional view of therapeutic catheter 803 of FIG. 9. In FIG. 10 therapeutic catheter 803 is shown disposed within a blood vessel 883. In the embodiment of FIG. 10, laterally flexible portion 807 of therapeutic catheter 803 has been urged into a generally curved shape having radius of curvature 863.

Inner shaft 835 is slidingly disposed within catheter lumen 833 and inner shaft 835 may be advanced distally so that point 843 is disposed distally of the distal end of laterally flexible portion 807. With laterally flexible portion 807 of therapeutic catheter 803 having a generally curved shape, point 843 may be directed toward a plaque deposit 865. In the embodiment of FIG. 10, point 843 of inner shaft 835 has pierced a wall of plaque deposit 865 and injection port 845 is disposed within a core 867 of plaque deposit 865. In a preferred embodiment, injection port 845 is fluidly coupled to a fluid source via an injection lumen 847. Fluid from the fluid source may be injected into the core 867 of plaque deposit 865 by urging the fluid through injection lumen 847 and injection port 845. The fluid injected into the plaque deposit preferably includes lipid/plaque stabilizing drugs.

Figure 11:
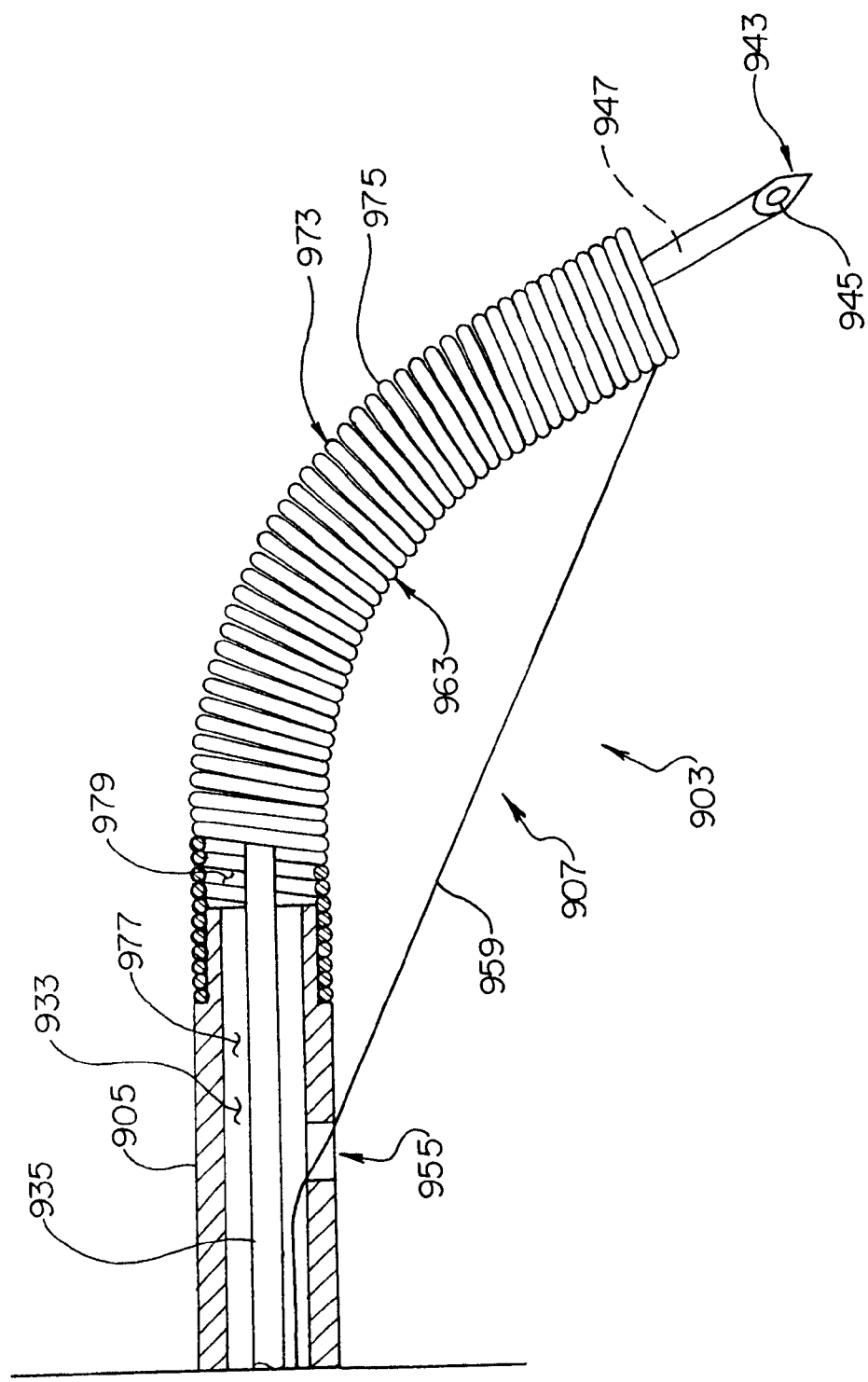
FIG. 11 is a partial cross sectional view of a therapeutic catheter in accordance with an additional embodiment of the present invention.

FIG. 11 is a partial cross sectional view of a therapeutic catheter 903 in accordance with an additional embodiment of the present invention. Therapeutic catheter 903 comprises an outer shaft 905 and a laterally flexible portion 907 that is fixed to a distal end of outer shaft 905. In the embodiment of FIG. 11, laterally flexible portion 907 comprises a coil 973 having a plurality of turns 975. In a preferred embodiment, adjacent turns 975 are disposed in close proximity to one another. In a particularly preferred embodiment, adjacent turns 975 contact each other across substantially their entire length. In this particularly preferred embodiment, coil 973 has a high level of longitudinal pushability and a high level of lateral flexibility.

Therapeutic catheter 903 includes a catheter lumen 933 defined by outer shaft 905 and coil 973. In FIG. 11, an inner shaft 935 is shown slidingly disposed within catheter lumen 933. In the embodiment of FIG. 11, inner shaft 935 forms a point 943 proximate the distal end thereof. Inner shaft 935 defines an injection port 945, proximate point 943 and an injection lumen 947 in fluid communication with injection port 945. In a preferred embodiment, injection port 945 may be fluidly coupled to a fluid source via injection lumen 947. Fluid from the fluid source may be injected into a plaque deposit by piercing a wall of the deposit with point 943 so that injection port 945 is disposed within a core of the plaque deposit. Fluid from the fluid source may then be urged through injection lumen 947 and injection port 945. The fluid injected into the plaque deposit may preferably include lipid/plaque stabilizing drugs.

In FIG. 11, it may be appreciated that therapeutic catheter 903 includes a pull wire 959 that extends through an aperture 955 defined by outer shaft 905. A distal end of pull wire 959 is fixed to coil 973 of therapeutic catheter 903 proximate a distal end thereof. A proximal portion of pull wire 959 preferably extends proximally beyond a proximal end of outer shaft 905. Pull wire 959 may be used to change the shape of coil 973 of therapeutic catheter 903. In a preferred embodiment, coil 973 of therapeutic catheter 903 may assume a generally straight shape and may also selectively assume a generally curved shape. In the embodiment of FIG. 11, therapeutic catheter 903 is shown having a generally curved shape with a radius of curvature 963.

Inner shaft 935 is slidingly disposed within a catheter lumen 933. In FIG. 11 it may be appreciated that catheter lumen 933 includes a shaft lumen 977 defined by outer shaft 905 and a coil lumen 979 defined by coil 973. Inner shaft 935 may be advanced distally so that point 943 is disposed distally of the distal end of coil 973. Point 943 of inner shaft 935 may be directed toward a plaque deposit 965, for example, by urging coil 973 into a generally curved shape. Coil 973 may be urged into a generally curved shape, for example, by applying a pulling force to the proximal portion of pull wire 959.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention.

What is claimed is:

1. An elongate medical device for mapping vulnerable plaque deposits within a blood vessel, comprising:

an elongate shaft having a proximal end and a distal end;

at least one infra-red temperature sensor fixed to the elongate shaft proximate the distal end thereof; and an inflatable balloon for receiving a gas inflation medium, the inflatable balloon encompassing said at least one infra-red temperature sensor.

2. The elongate medical device of claim 1 further comprising a gas inflation medium disposed within the inflatable balloon.

3. The elongate medical device of claim 1, wherein said at least one infra-red temperature sensor is coupled to a switching device.

4. The elongate medical device of claim 3, wherein the switching device comprises a diode.

5. The elongate medical device of claim 3, wherein the switching device comprises a transistor.

6. The elongate medical device of claim 1, wherein said at least one infra-red temperature sensor comprises a resistor.

7. The elongate medical device of claim 1, wherein said at least one infra-red temperature sensor comprises a thin film resistor.

8. A method for mapping vulnerable plaque deposits within a blood vessel, the method comprising the steps of:

providing an elongate medical device including an elongate shaft having a proximal end and a distal end, at least one infrared temperature sensor fixed to the elongate shaft proximate the distal end thereof, and an inflatable balloon for receiving a gas inflation medium, the inflatable balloon encompassing the at least one infra-red temperature sensor, inserting the distal end of the elongate shaft into a lumen of a blood vessel, and positioning the inflatable balloon and the at least one infra-red temperature sensor proximate a plaque deposit;

inflating the balloon with the gas inflation medium; and sensing the temperature along the vessel wall with the at least one infra-red temperature sensor.

9. The method according to claim 8, wherein said at least one infra-red temperature sensor is coupled to a switching device.

10. The method according to claim 8, wherein the switching device comprises a diode.

11. The method according to claim 8, wherein the switching device comprises a transistor.

12. The method according to claim 8, wherein said at least one infra-red temperature sensor comprises a resistor.

13. The method according to claim 8, wherein said at least one infra-red temperature sensor comprises a thin film resistor.

* * * * *